United States Patent [19]

Lambert

[11] Patent Number: 5,012,522
[45] Date of Patent: Apr. 30, 1991

[54] AUTONOMOUS FACE RECOGNITION MACHINE

[75] Inventor: Laurence C. Lambert, Bedford, Mass.

[73] Assignee: The United States of America as represented by the Secretary of the Air Force, Washington, D.C.

[21] Appl. No.: 282,227

[22] Filed: Dec. 8, 1988

[51] Int. Cl.$^5$ .......................... G06K 9/00; G06K 9/20; H04N 7/18; G07D 7/00

[52] U.S. Cl. ......................................... 382/2; 382/48; 358/105; 340/825.34

[58] Field of Search ........................... 382/2, 65, 48, 1; 358/104, 105; 340/825.34, 825.31

[56] References Cited

U.S. PATENT DOCUMENTS

| | | | |
|---|---|---|---|
| 3,999,006 | 12/1976 | Takeuchi et al. | 358/85 |
| 4,109,237 | 8/1978 | Hill | 382/2 |
| 4,449,189 | 5/1984 | Feix et al. | 364/513.5 |
| 4,625,329 | 11/1986 | Ishikawa et al. | 382/1 |
| 4,739,401 | 4/1988 | Sacks et al. | 382/1 |
| 4,773,024 | 9/1988 | Faggin et al. | 364/513 |

OTHER PUBLICATIONS

Leung, "Human Body Motion Segmentation in a Complex Scene", Pattern Recognition, vol. 20, #1, 1987, pp. 55-64.

Smith, Edward J., "Development of an Autonomous Face Recognition Machine", Masters Thesis, Doc. #AD-A178852, Air Force Institute of Technology, Dec. 1986.

Routh, Richard L., "Cortical Thought Theory: A Working Model of The Human Gestalt Mechanism", Doctoral Thesis, Document #AD-A163215, Air Force Institute of Technology, Jul. 1985.

*Primary Examiner*—Leo H. Boudreau
*Assistant Examiner*—Michael R. Cammarata
*Attorney, Agent, or Firm*—William G. Auton; Donald J. Singer

[57] ABSTRACT

A machine is disclosed that is capable of locating human faces in video scenes with random content within two minutes, and capable of recognizing the faces that it locates. The machine uses images obtained from a video camera and is insensitive to variations in brightness, scale, focus, and operates without any human intervention or inputs. When a motion detection feature is included, (one of its options), the location and recognition events occur in less than 1 minute. One embodiment of the system uses: a camera, a Micro-Vax computer, an analog-go-digital A/D converter, and a hard copy print out to process video scenes with random content using an original computer program to locate human faces and identify them. In operation, the camera converts the video scenes into an analog electrical signal, which is converted into digital and forwarded to the computer. The computer performs an original pattern recognition algorithm to search for facial components, identify a gestalt face, and compare the gestalt-face's detected facial characteristics with a stored set of facial characteristics of known human faces, to identify the face thereby.

1 Claim, 2 Drawing Sheets

AUTONOMOUS FACE RECOGNITION MACHINE

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to pattern recognition systems, and more specifically the invention pertains to a machine of locating human faces in video scenes with random content, and capable of recognizing the faces that it locates.

Personal access control systems have been implemented using visual recognition for identification of individuals. Visual recognition systems use characteristic portions of the human body for identification purposes. Typical of this type of access control are fingerprint recognition systems and facial feature recognition systems. One such system is described in U.S. Pat. No. 4,109,237, entitled "Apparatus and Method for Identifying individuals through the Retinal Vasculature Patterns", issued Aug. 22, 1978. This system uses a method of scanning the individual's eye with a light source arranged in a selected pattern and detecting that portion of the light source pattern which is reflected from the person's retina, thereby locating each intercept of the light source pattern with a blood vessel. The intercept pattern thus obtained is then compared with stored intercept patterns previously obtained from individuals who are cleared for access. Personal access control systems using visual recognition alone demand an even higher level of technical effort and sophistication than acoustical recognition systems.

The problem with identification systems like the one described above is that it requires a cooperative individual who is willing to subject himself to a retinal scan. The task of providing a system which locates human faces in video scenes with random content, and then identifies the faces it locates is alleviated to some extent, by the systems disclosed in the following U.S. Patents, the disclosures of which are specifically incorporated herein by reference:

U.S. Pat. No. 4,449,189 issued Feix;
U.S. Pat. No. 3,999,006 issued Takeuchi et al;
U.S. Pat. No. 4,773,024 issued Faggin et al; and
U.S. Pat. No. 4,625,329 issued Ishikawa.

Perhaps the most significant of the above-cited references is the Feix patent. The Feix reference discloses a personal access control system which uses speech and face recognition. It relies on both a voice signature as well as the identification of the facial features of the speaker.

The face recognition system of the above-cited Feix system resembles earlier personal identification systems in that it requires a cooperative person who participates in his identification through a combination of both speech and face recognition. The voice signature of interrogated person uttering a key word into a microphone is compared in a pattern matcher with the previously stored voice signature of a known person uttering the same key word to obtain a first similarity score. At the same time, when a key event in the utterance of the key word by the interrogated person occurs, a momentary image of that person's mouth region onto which a grid pattern has been projected is optically recorded and compared with the previously stored corresponding momentary image of the same known person to obtain a second similarity score. The two similarity scores are analyzed to verify that the identity of the interrogated person is that of the known person.

A Face Recognition Machine (FRM) was developed at the Air Force Institute of Technology (AFIT) by Robert Russel in 1985. The FRM was based on Cortical Thought Theory (CTT) which proposes a new model of how a human brain processes information. Richard Routh developed and presented CTT as a doctoral dissertation at AFIT in 1985. CTT proposes that information is displayed as a two dimensional image on the brain. The brain then extracts the essential information (the essence of the image) as a two-dimensional vector, called a "gestalt". The gestalt is the only information that is passed to the higher levels of the brain for processing according to Mr. Routh in his article entitled "Cortical Thought Theory: A Working Model of the Human Gestalt Mechanism." PhD Dissertation, AFIT/DS/EE/85-1, Air Force Institute of Technology, DTIC Document, July 1985. Here, the FRM reduces facial images to gestalts and then compares the gestalt to a data-base in an attempt to recognize the face.

In 1986 an AFIT student added automatic face location and windowing algorithms to the FRM to eliminate human influence on the recognition process (Smith, 1986). The face locator was slow and recognition was less accurate because only the internal features of the face (eyes, nose, mouth) were used, but the question this student was trying to answer was, "Can a machine, entirely on its own, determine whether or not a persons'face is in a picture and if so, can it determine to whom the face belongs? "The answer is "yes" and the result of the student's thesis effort became the Autonomous Face Recognition Machine (AFRM) as developed by Edward J. Smith, and as documented in his thesis entitled "Development of an Autonomous Face Recognition Machine." Masters Thesis, AFIT/GE ENG/86D-36, Air Force Institute of Technology, DTIC Document, December 1986.

The present invention began after an evaluation of the AFRM location and windowing algorithms with the goal of improving recognition score and speed. Both the score and speed were reduced with the addition of the autonomous scene analysis (location and windowing) algorithms in 1986, and human influence was eliminated. The goal of this effort was to reduce the 5 to 30 minute scene analysis time as much as possible while bringing the recognition score back up to a least what was possible when human influence was allowed.

Improvement of the windowing algorithms should improve overall recognition accuracy. There are several windows on the facial scene that will be tested as possible replacements for the windows that have little affect on the recognition score. Going back to a whole-head approach used in 1985 should also improve accuracy over the internal feature approach now used. The only reason internal features are now used is the inability to separate the edges of the head from a random background. This invention investigates two possible solutions to this problem. The first is to apply an elliptical mask to a scene centered around the location of the face with a size proportional to the size of the internal features. This results in a larger area of the face being made available to the recognition algorithm. The second solution is to apply a Moving Target Indicator (MTI) algorithm to a series of input scenes prior to scene analysis. This may allow better detection of the edge of the head.

Improvement of the location algorithm may speed up the scene analysis, however the major improvement in speed will be gained by re-hosting the AFRM on a new Micro-VAX computer and its related equipment.

While identification of cooperative individuals who participate in the identification process represents a breakthrough in the art, a need remains to provide an improved system capable of locating human faces in video scenes with random content, then recognizing the faces that it locates. The present invention is intended to satisfy that need.

SUMMARY OF THE INVENTION

The present invention is a machine capable of locating human faces in video scenes with random content, and capable of recognizing the face that it locates. The machine uses images obtained from a video camera and is insensitive to variations in brightness, scale, focus, and operates without any human intervention or inputs. When a motion detection feature is included, (one of its options), the location and recognition events occur in less than 1 minute.

One embodiment of the present invention accomplishes these functions in an image processing system which uses: a video camera, a monitor, a computer, Micro-Vax Intech board, and Tektronics hardcopy unit. The video camera is electrically connected to the computer by Micro-Vax Intech board, which acts as a computer interface and digitizes the signals from the camera. The computer performs the image processing functions discussed above using an original program to allow the monitor and hard copy unit to output the identity of the face recognized by the system.

It is an object of the present invention to provide an autonomous system which will find and recognize a human being in a video scene without knowledge of the person's location or size.

It is another object of the present invention to provide a pattern recognition system which functions as a personal identification system while automatically correcting for natural variations in a video scene environment.

These objects together with other objects, features and advantages of the invention will become more readily apparent from the following detailed description when taken in conjunction with the accompanying drawings wherein like elements are given like reference numerals throughout.

DETAILED DESCRIPTION OF THE PREFERRED EMBODIMENT

The present invention is a machine capable of locating human faces in video scenes with random content, and capable of recognizing the faces that it locates.

Cortical Thought Theory (CTT), developed by Captain Richard Routh, proposed a model of the human brain that was based on primitives of analogy as opposed to primitives of deduction. Routh described how primitives of analogy could be used to achieve human-like classification of data and human-like recall or, "direct memory access". The classification, or single unique identification of an object, was called the "gestalt" of the object.

In 1985 Robert L. Russel applied CTT to the problem of face recognition. The results of Russel's work increased the credibility of CTT as a model of human sensory processing. In 1986, Edward Smith added an automatic face location algorithm to Russel's face recognizer to make the recognition process independent of operator influence.

Figure 1:
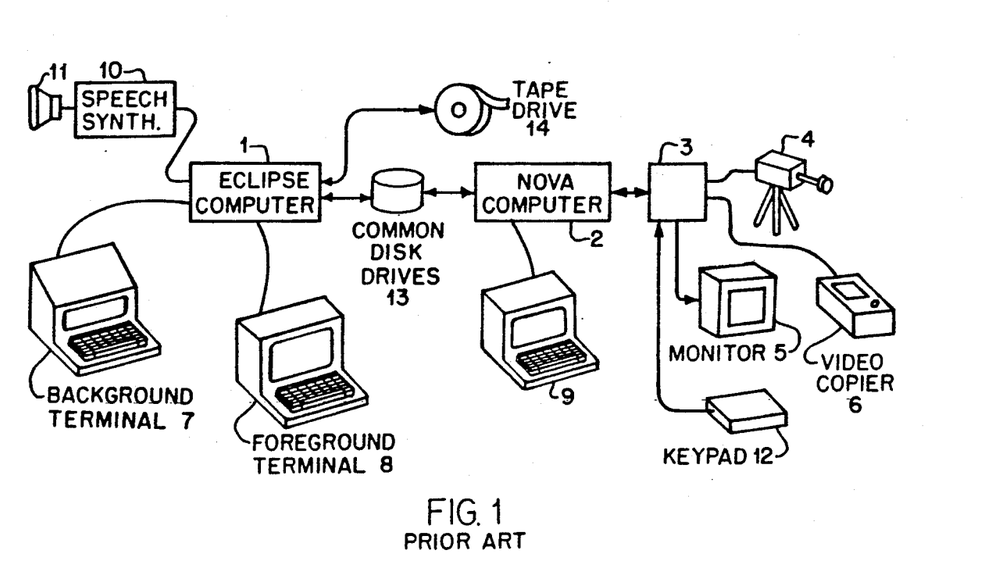
FIG. 1 is an illustration of a prior art face recognition system.

The reader's attention is now directed towards FIG. 1, which is a prior art face recognition machine (FRM) developed by Robert Russel in 1985, as presented in the above-cited Smith reference. The FRM of FIG. 1 is a two-computer system which accomplishes face recognition using: an Eclipse computer 1, a Nova computer 2, a video processing board 3, a camera 4, a video monitor 5, a video copier 6, a background terminal 7, a foreground terminal 8, a Nova computer terminal 8, a speech synthesizer 10, a speaker 11, and keypad 12. All of the equipment is commercially-available, and some of the units are listed below in Table 1.

TABLE 1

1. Data General Eclipse S/250 Computer System
2. Data General Nova 2 Computer System
3. Octek 2000 video Processing BOard
4. Dage 650 Video Camera
5. Panasonic WV-5490 Monochrome Monitor
6. Tektronix 4632 Video Hard Copy Unit The Nova computer 2 was used for image acquisition and display, and the Eclipse 1 was used for the large amount of numerical processing required by the gestalt calculations. The two computers shared a common disk drive 13 and communicated via flag files stored on disk. In many cases these flag files existed in name only to tell one computer that a process was finished on the other. In some cases the files contained data that was to be passed from one computer to the other. Software for the recognizer was written in Fortran IV and Fortran V and extensive use of subroutine swapping and overlay techniques were employed due to the small main memory, approximately 28 K bytes, available for running programs.

Figure 2:
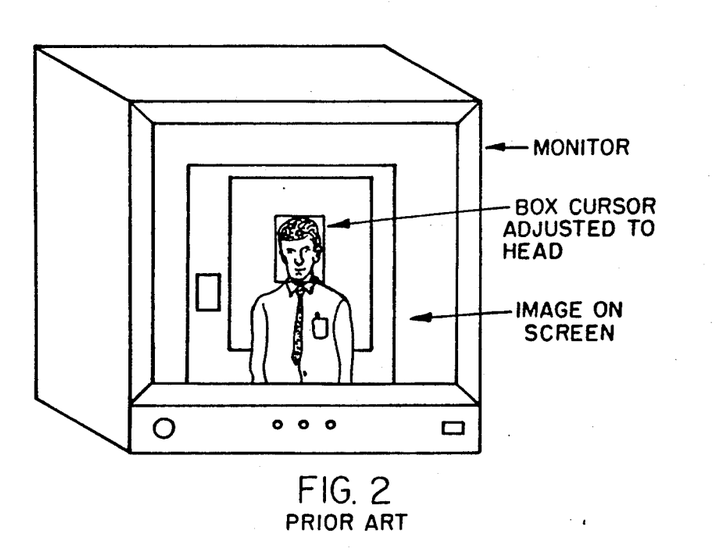
FIG. 2 is an illustration of the cursor adjustments required for the system of FIG. 1 to capture and identify a human face from the background using the Russel system.

The equipment shown in FIG. 1 was used to acquire and process images. The Octek 2000 video processing board 3 connected to the Nova 2 was used to acquire four-bit images from a black and white video camera 4. Once acquired, an image could be stored to disk, displayed on the monitor or printed on the video hardcopy unit 6. In Russel's system, image acquisition was accomplished with a fixed camera setup and layout. The background was a plain piece of cardboard and the camera had to be calibrated to the brightness of this board. After taking a picture, the user provided the computer with the coordinates of the face by manually adjusting a box-shaped cursor around the subject's head as shown in FIG. 2. In order to recognize the face, the computer had to divide the face into several separate windows. Success in locating and windowing the face depended upon the contrast found in the scene and so the input scene had to be pre-processed to obtain a constant contrast value.

Preprocessing consisted of a contrast enhancement algorithm that sampled the pixel values in the center of the face and adjusted the contrast of the whole face based on the average of the center pixels.

In Smith's system images were acquired using the same equipment Russel used, but instead of providing the computer with the face coordinates, the computer ran an automatic face location algorithm. The Only requirements imposed on image acquisition was a camera calibration and the background was allowed to vary.

Success in locating and windowing the subject's features still required a constant contrast value, so Russel's contrast enhancement algorithm was still used. The algorithm was applied to the scene after the face locator found most of the features of a face, in order to help it find the rest of the features. Then a slightly modified version of the contrast enhancement algorithm was applied to the face to improve the accuracy and repeatability of the windowing and recognition algorithms.

There are two requirements of the face location algorithm used in the Autonomous Face Recognition Machine (AFRM). The first is to ensure that only faces are passed to the recognition algorithm and that all other parts of the input scene are discarded. The second requirement is to find specific features on the face that need to be used by the windowing algorithm.

In Russel's FRM the first (face location) requirement was met by having the user position a block around the face as shown in FIG. 2. The second (feature location) requirement was met by using an automatic feature location algorithm. The accuracy of the feature locations were dependent on the contrast of the input image, the set of rules within the location algorithm, and sometimes a manual correction entered by the user.

In Smith's AFRM the face location requirement was accomplished using an automatic "facefinder" algorithm. Feature location was accomplished as a part of the face location process. The facefinder works by searching an input image for certain facial characteristics called "signatures". The facial signatures are present in most facial images and are rarely present when no face is present. Smith presented test results in his thesis that show how "face specific" the facefinder was.

The facial signatures are made up of the brightness variations in a scene that are consistently found when a face is present. The "eye signature" is made up of the three brightness maxima found around the eyes (one between and one to each side of the eyes) and the two brightness minima found in the center of the eyes. These maxima and minima form a characteristic "W" shape when the brightness on a line through the eyes is plotted. Smith also defined a "nose/mouth signature".

The development and calculation of the facial signatures was based in part on similar work in which specific features in mug file images were located using a signature technique. The signatures were generated by adding pixel values in each column of the image and plotting the results. Characteristic maxima and minima appeared at the center and edges of the face. Smith generated his facial signatures by extracting columns from an image and plotting the results of a one-dimensional gestalt calculation for each column.

After convolving the signatures with gaussian function to smooth them, Smith applied a set of limits to determine if the signatures represented a face. The limits defined allowable variations in maxima and minima, the maximum distance ratios between various points on the signature, and the maximum variation of the slopes between maxima and minima.

Figure 3:
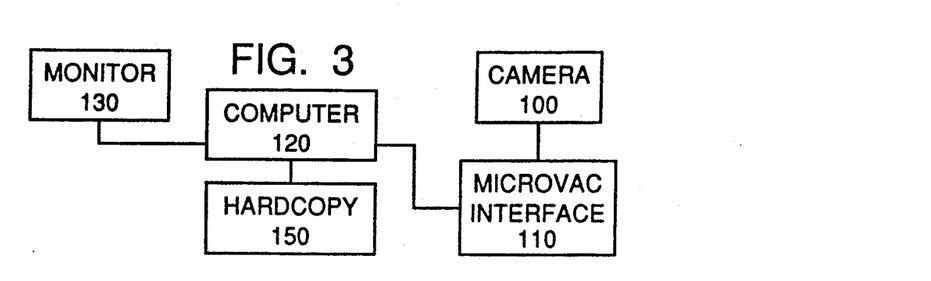
FIG. 3 is a block diagram of the components of the face recognition system of the present invention.

The reader's attention is now directed towards FIG. 3 which is a block diagram of an embodiment of the present invention. The system of FIG. 3 is an image processing system which use a video camera 100, a Micro-Vax interface board 110, Micro-Vax II computer 120, a monitor 130 and a hard copy printer unit 150 in order to identify people in the video scene captured by the camera 100 using original software which is described in detail below. The system of FIG. 3 is just one example of the application of the present invention, and uses equipment which is commercially-available. For example, one version of this system included a Micro-Vax Intech board, Dage 650 camera, Deanza video monitor, and a Tektronics hardcopy unit. The video camera 100 is electrically connected to the computer 120 by the Micro-Vax Intech board 110, which acts as a computer interface and digitizes the signals from the camera. The computer 120 performs the image processing functions discussed above using an original program to allow the monitor and hard copy unit to display the identity of people recognized in the video scene.

Figure 4:
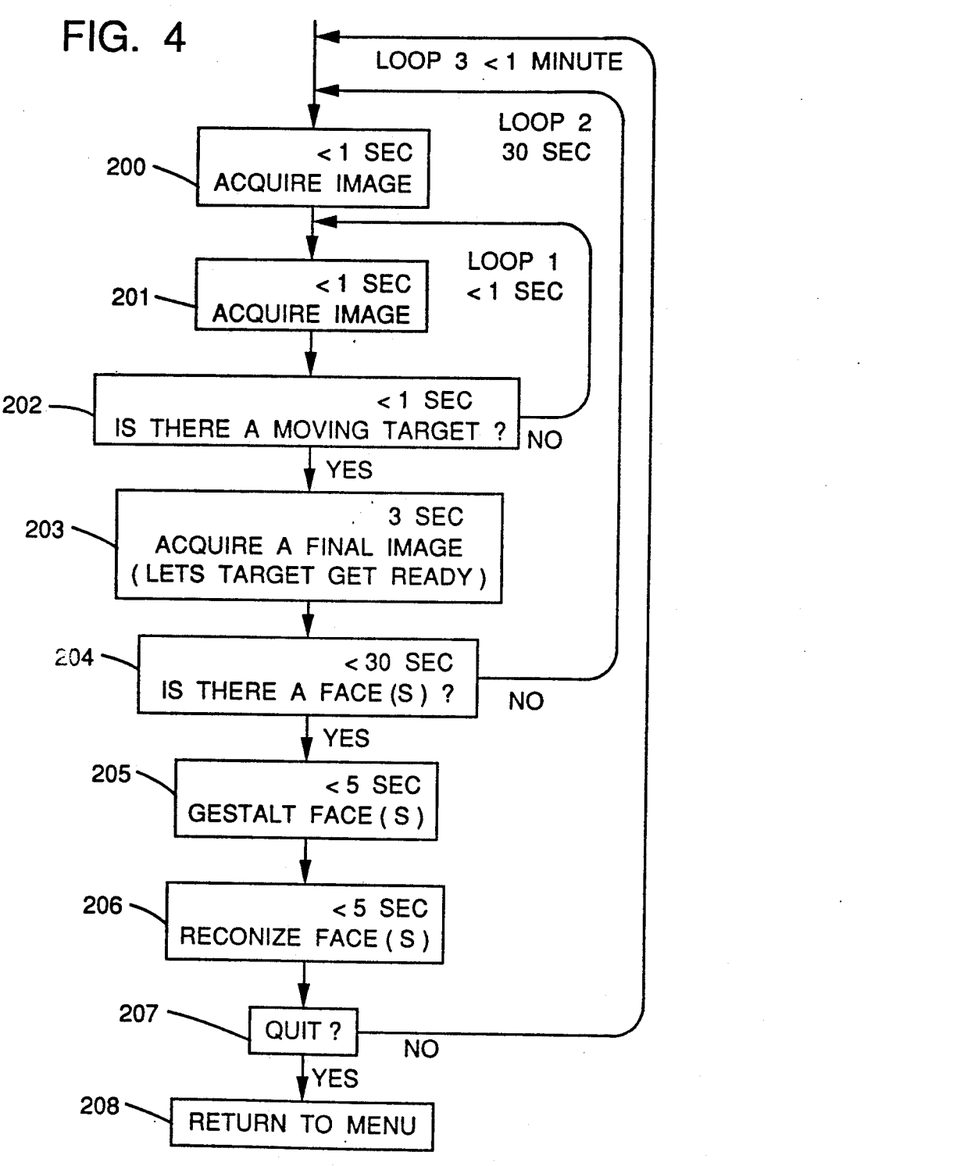
FIG. 4 is a block diagram of the total system option algorithm used in the process of the present invention.

Before proceeding to a description of the software programs, it is important for the reader to understand the characteristics of the pattern recognition process used in the present invention to recognize and identify human faces in a video scene. Therefore, the reader's attention is now directed towards FIG. 4, which is an illustration of an algorithm of the present invention which searches for, recognizes, and identifies a human face in the video scene provided by the camera 100 of FIG. 3. The object code that implements this algorithm will be provided below, but the purpose of FIG. 4 is to discuss the pattern recognition principles used in the present invention.

When the object code is loaded into the Micro-Vax II computer 120 of FIG. 1, the monitor of the computer will display the Autonomous Face Recognition Machine (AFRM) menu listed below as Table 2. When the demonstration item of the main menu is selected, and when the total system option is selected, the system performs the algorithm of FIG. 4 in the manner discussed below.

TABLE 2

AFRM Menu Structure

Main Menu 
1: Acquire Images
2: Find Faces
3: Gestalt and Identify/Save
4: Display Contents of Dbase
5: Delete a Subject
6: Delete an Image
7: Train
8: Demonstration ⟶  Demonstration 
0: Quit

Acquisition of Images 
0: Return to Main Menu

1: Stationary Target
2: Moving Target
3: Load Image from Memory
4: Save Image in [FACE]

5: Set Camera Port
6: Camera Check
7: Re-Initialize Hardware

Demonstration 
0: Return to Main Menu

1: Identify a Person
2: Total System

The process of FIG. 4 begins as the computer 120 acquires and stores an image 200 from the camera 100 of FIG. 3. After a one second interval, the computer acquires a second image 201 from the same scene and compares it with the first image to determined if there is movement 202. This is easily accomplished as follows.

Assuming a constant illumination for the scene, the second image acquired in step 201 should be identical with the first image acquired in step 200 in the absence of movement. That is, all of the digitized pixels in the second image that indicated illumination would indicate illumination in the first image; and all the darkened pixels in the second image would be darkened in the first image. The reason for this is that if there is no movement in a scene that is subject to constant illumination, there should be no change in the image. Therefore, as part of the present invention, a moving target indicator (MTI) algorithm was added to the AFRM as the first step in processing the scene, with the following assumption:

"Faces may be present on moving targets but are never present when there is no motion. (The motion must occur between the acquisition of two consecutive scenes and the user will be allowed to bypass the MTI step in order to process previously stored or "still" photos)."

Using this assumption, the time required to locate a face is greatly reduced by searching only a portion of the scene. In addition, the MTI algorithm might enable the system to distinguish the separation of the edges of the head from the background.

Once movement has been detected 202, the system will wait three seconds, and acquires a final image 203 whose contents will be searched 204 to find a human face. The source code which performs this is called "FACE.C", and it contains all the algorithms, all the code necessary for maintaining a facial database, and the menu structure shown in Table 2. When a user logs on, the main menu is displayed on the computer screen. This menu provides access to the individual AFRM algorithms and access to the database and demonstration options that will be described below.

Please note that the video equipment shown in FIG. 3 actually captures the image of the subject by snapping a picture in about 1/30th of a second in step 203. If other equipment is used, the amount of time used to take the picture may vary, but the use of a relatively short exposure time in actually taking the picture tends to produce a "stop motion" image which reduces the effects of human motion on the acquired image.

The AFRM menu structure is set up so that a user can run each algorithm independently of all the others. In addition, an option called "Total System" is provided that runs all the algorithms in series as shown in FIG. 4. No operator inputs are required once this option is selected except for selecting which camera to use and when to quit. FIG. 4 shows the time spent in each algorithm and the time required for each loop. The subroutine in FACE.C that is represented by this flowchart is called "AFRM()".

In order to recognize a subject, the AFRM must be given an image of the subject's face with no significant (less than 5 degrees) tilt or rotation of the subject's head. This means that a frontal view of the person's head is necessary for recognition. With no other constraints imposed on the image, the AFRM is required to locate and recognize the subject. In order to help the AFRM accomplish this task quickly, accurately, and consistently, several preprocessing steps can be performed on the input image.

In Russel's FRM, the user was required to identify the location of the face by positioning a box-shaped cursor on the video monitor. The only part of the image used by the FRM was the part inside the box. Smith provided the whole scene to the AFRM and added an automatic location algorithm to locate a randomly positioned face in a random background. This location algorithm could take anywhere from 5 to 30 minutes to find the face in the scene which must be accomplished prior to recognition of the face.

In step 204 of FIG. 4, the computer performs a pattern recognition program to search for a human face in the video scene. As the attached programs show, this pattern recognition begins by searching the image for an easily recognizable features of the human face: a pair of eyes. If no eyes are located in the scene, the computer will decide that no face is contained in the image, and the program will return back to step 200, and reacquire a new image.

A pair of eyes are recognized as a pair or comparatively dark adjacent elipses, which form an eye signature. If one finds two dark objects with nearly the same size, one next to the other, then a possible pair of eyes is detected. A "dark" object in this case is an object with a light area all the way around it. This eliminates false alarms in scenes. The only task the face location algorithm has is checking for two dark objects (nose, mouth) below and between two others that are side by side (eyes).

The new location algorithm is reasonable model of a human. It is hard for a human to find a face in a scene given one line of data at a time, but easy if given small regions of the scene. Research into eye scanning patterns show that it is likely that people are evaluating small areas in a scene. If the brain can determine whether a dark object is present in a small area of a scene, and remember where that area is in relation to all other areas, then it can easily recognize more complicated objects in the scene given some simple rules. For example, a face decision rule would be:

"If there is a dark object;
if, there is a second one beside it;
if there is a third below and between them;
if there is a fourth directly below the third;
then there is a face."

If a pair of eyes are located in the scene, the pattern recognition program will then search for nose and mouth in proximity, with the eyes to constitute a gestalt face 205. As mentioned above, a prerequisite for recognition of a subjects face is a frontal view of the subject'- whole head. No information from behind the edges of the head is allowed because this information comes from an uncontrolled background. The MTI algorithm can separate a moving target from the background, but it is not quite good enough to sue with only brightness values from a black and white image. Smith chose to provide only the internal features of the head and this resulted in a lower recognition accuracy. The technique presented here, called an elliptical mask, is designed to provide the recognition algorithm with an approximation to a whole-head view of the subject (providing less information than the whole-head approach but more information than the internal feature approach.) The goal is to give the face recognizer as much information about the subject as possible without adding uncontrollable background data. In order to create an elliptical mask, the following assumption is necessary.

"The head is elliptical (available software allows easy creation of only ellipses, circles or rectangles). The size of the head can be approximated if the size of the internal facial features are known."

Using this assumption and Smith's automatic face location algorithm (to find and measure the internal features), the size of the subject's head is approximated. An ellipse of this size is drawn around the face and everything outside the ellipse is cleared to a constant brightness value. This new image is fed into the recognition algorithm with a whole-head on a pristine background. Testing the elliptical mask algorithm yielded the following result. The ratio between facial feature size and head size is not a constant. Because of this result, the ellipse size and center location has to be adjusted so that it does not extend beyond the edge of any subject's head.

When the new face location algorithm was tested on the Micro-VAX, the following results were observed. The location algorithm finds faces in an input scene in less than 2 minutes for the configuration of FIG. 3, subject to the following constraints. When the Dage 650 video camera listed in Table 1 is used, the input scene size is 512 by 480 pixels.

The system of FIG. 3 is able to locate at least one face in an input scene, and perhaps up to 60 faces when they present a full, unobstructed frontal view to the camera. The reason for this is that the minimum facial size necessary for recognition is about 64 by 64 pixels. Since this minimum facial size represents about 1/60th of the input scene size of 512 by 450 pixels (for the equipment depicted in FIG. 3) the total number of faces that the system could hypothecally identify is 60 faces. This amount could vary as different equipment is used. Therefore, the user is advised that he may have to determine empirically the minimum facial size characteristic if other equipment is used as opposed to that shown in FIG. 3.

As mentioned above, the system has a limit of less than about five degrees on the amount of tilt and rotation that can be tolerated in a subject's head with respect to the camera. The reason for this limit is that excessive tilt and rotation of the subject's head will produce a foreshortening of the head's image within the perspective of the camera. Human motion does not appear to present a problem to the system when the equipment listed shown in FIG. 3. More specifically, the video equipment actually snaps the picture used by the invention in about 1/30th of a second. This effectively serves as a "stop motion " picture of the subject which does not seem to be effected by normal human motion. The user is advised that the effects of human motion, rotation, and tilt of the subjects may have different limitations when equipment other than that shown in FIG. 3 is used, and these effects would have to be determined empirically. This includes time to preprocess, time to locate features, and time to store each face to a disk.

The location algorithm is scale invariant. As long as features sizes match each other within a face, it doesn't matter what the overall sizes are as long as they are under a maximum defined limitation.

The location algorithm is brightness invariant. The brightness normalization algorithm takes care of variations in the input scenes. The algorithm is sensitive to eyeglasses and mustaches if they get in the way of separating facial features.

The algorithm allows slight head rotation and variations in lighting direction (as long as lighting is still from somewhere above the subject).

Once a complete face is identified in the image 205, the data of the scene will be compared with data base which was stored in the computer in order to maintain the gestalt files of all subjects entered into the AFRM. This includes the files for subjects that the AFRM is trained with, and extra files used for testing the recognition capabilities of the AFRM. When the AFRM is not running, all the gestalt data are kept in two files called "TRAIN.DAT;1" and "OTHERS.DAT;1." These files are ASCII test files, so they can be displayed on the computer screen and printed to a printer. The data base software is contained in subroutine "MENU1" and is supported by the following subroutines which are all contained in FACE.C:

| COPYFILE | GETINT |
| DEL | READFILE |
| DISPLAY | WRITEFILE |

When the AFRM is first activated, the two disk files are rad into arrays in the memory. The contents of these arrays are modified using Main Menu options 3 through 7 while the AFRM is running and when option 0 (Quit) is selected, any modifications are written into the disk. It is important that the AFRM is terminated only by using the Quit option, because all other methods of terminating the program (CTRL-C, CTRL-Y, etc) will prevent the modified array data from being stored onto a disk.

The arrays used to hold gestalt data are implemented using C structures so that subject names, file versions and gestalt values can all be held in the same array. The two structures are called TLIST and ILIST and the contents of these structures are global, available to all the subroutines that need to access them. Main menu options allow the user to add to (by training), subtract from (delete trained subjects or individual images), and display the contents of the structures.

The gestalt data files are stored on disk in a directory called [FACE.DBASE] along with all the picture files. The picture files are stored by subject name and an extension that identifies the status of the subject: IMG files are pictures that the AFRM has not been trained with, and PIC files are pictures the AFRM has been trained with. These extensions are automatically changed by the AFRM when a subject is moved from one area of the database to the other. The picture files are also stored with version numbers that match the version numbers in the data files, so the gestalt file is always linked to the photo it was obtained from.

Once the face has been identified the pattern recognition subroutine will quit 207 and return to the menu 208. At this time, the monitor 130 will display the menu of Table 2, and the hard copy printer 150 can print out the identity of the face from the memory of the computer 120 of FIG. 3. If the face is not recognized the computer will indicate this, and return to the step of acquiring another image 200. The reason for this is because of the possibility that the person is recognizable by the computer, but the facial angle or lighting in the image might not have provided an image that conformed with the gestalt-face stored in the computer memory. In other words, the system simply takes a second look, and tries again to identify the subject.

The Computer Program Listing Appendix, which is presented below, contains the entire face recognition code necessary to use the present invention. When this code is input into the Micro-Vax II computer of FIG. 3, and when that computer is electrically connected to the commercially-available equipment of FIG. 3 the result is the autonomous face recognition system of the present invention. The code contains comments which provide a description of the operations that are being accomplished as the code is run through the computer.

```
if (fy ( ( sy + size) ) return(0)
for (x=size-1; x(= 511; x=x+size)   /* find left side */
  for ( y = 0; y ( 255; y=y+size)
  z = brpixel(x,y);
  if (mode == 6) z z & 63;
  if(z )= thresh)
     sx = x = 512;
     x = y 512;

if (sx == -1) return(0);
for x = 512-size; x) (sx + size-1) x = x - size) /
  for ( y = 0; y ( 255; y = y + size)   find right side */
  z = brpixed(x,y);
  if (mode == 6) z = z & 63;
  if (z ) = thresh)
    fx = x + size-1;
    x = -1;
    y = 512;

if (fx ( (sx + size)) return(0);
return(1);

/*****************************************************************/
#define A0 (short int)a0(i) /* These are the transformations used in the   *
#define a0(i) (i & 0x003f)  /* feedback lut for the real time subtraction  *
#define A1 (short int)a1(i) /* demo.  This software was created by using   *
#define a1(i) (i & 0x0fc0)fc) )) 6 /*the toolbox program (see FG-100 user's *
#define D0(i)  data &= 0xffc0; data 1 = (i & 0x003f);   /* manual chapt 7)   *
#define D1(i)  data &= 0xf03f; data 1 = ((i ((6) & 0x0fc));  /***************
#define INPUT 0x6000
#define ab(i) (((i) ( 0) ? (-(i)) : (i))

xform2(addr, initial)
 unsigned addr,initial;

register unsigned short i = addr;
register short int data = initial;
D1(A1 - A0);
return((unsigned)data;

xform2(addr,initial)
 unsigned addr,initial;

register unsigned short i = addr;
register short int data = initial;
D1(A0);
D0(abs(A1 - A0));
return((unsigned)data);

/*****************************************************************/
afrm()        /* A completely Autonomous Face Recognition Machine (AFRM)  */ int cam;
char t2[30],t3[30],stop,answer[1];
register unsigned j;
stop = 'n';
printf("/n Select camera port (0,1 or 2) )");
```

```
scanf("%d,&cam);
while (stop == 'n')
 cls();
 printf(" please wait...");
rtsubtract(0);
setcamera(cam);
setlut(0,0);
setinmux(6);
for (j=-0 j(0x1000; j++ write_lut(INPUT,j,xform2(j,read_read_lut(INPUT,j)));
cls();
printf("looking for target.");
snap(1);
snap(1);
while((isolate(8,6,32) != 1) snap(1);
printf("/n found targaet, acquireing 8 bit image.");
initialize();
setcamera(cam);
waitv();
snap();
nf = sx = sy = 0;
fx = 511;
fy = 255; /* presently isolataed() only looks for target in top */
if (facemap() == 1)      /* half so look for faces in top half */
 printf('/n found ');
 printf("%d,nf);
 if (nf == 1) printf(" face.");
 else printf("faces.");
 facerec(2);

printf("/n Do you wish to stop? (Y/N) )");
scanf("%s",answer);
if (answer[0] == 'Y' : answer[0] == 'y') stop = 'y';

return;

/*******************************************************************/
clear_cray()

int x,y;
for (y=1; y129; y++) for (x=1; x(129; x++ cray[x][y] = 0.0;
return;

/*******************************************************************/ cortran16()     /* Modified from CORTRAN16.FR 11/23/85 by R. RUSSEL */ int j,i,iwinmaxx,xtot,ytot,num;
     double c,bmax,ir3d,jr3d;
xtot = ytot = num = 0;
for (i=i; i(iy+2; i++)
 for (j=1; j(ix+2; j++)
  if (crayj][i] ) 100
  xtot += j;
  ytot += i;
  num++;

ir3d = (double) (ytot/num);
jr3d = (double) (xtot/num);
iwinmax = iy;                                    /* scale */
if (ix ) winmax) iwinmax = ix;
ir3d3 - ir3d*(128.0/(double)iwinmax) +0.5;
jr3d3 = jr3d*(128.0/(double)iwinmax) +0.5;
return;

/*******************************************************************/
del()

printf("n/n         Deleting files with reserved names.");
system("delete bnorm.img,*"); /* these names are reserved for facefinder */
syytem("delete orig.img,*");
return;

/*******************************************************************/
```

```
facerec(version)
int version;

char ch[2],t2[30],t3[30],t4[30p),t5[30];
 int w,l,m,n,p,dx,dy;
 if (nf !=0)
  cls();
  printf(" trying to recognize faces found...");
  for (m=1; m(nf+1; m++)
   t2[0] = '/0';                        /* create file names for face  # m */
   t4[0] = '/0';
 strcat (t2,"bnorm.img;/0");
 strcat (t4,"orig.img;/0");
 t3[0] = m + '0';
 t3[1] = '/0';
 strcat(t2,3);
 strcat(t4,t3);
 sx = 60;
 sy = 30;

printf("/n%s,t2),
 sciear(0,1);
 readim(sx,sy,200,200,t2,"nocom");    /* display bright_norm face */
 l = sy;
 while(brpixel(sx,l) !=0) l++;           /* get fx,fy values */
 fy = l - 1;
 l = sx;
 while(brpixel(s,sy) !=0) l++;
 fx = l - 1;
 dx = fx - sx;
 dy = fy - sy;
 cont_enhance(m)
 scale(m)
 text(70,10,0,1,0,t2);
 gestalt();                              /* gestalt values put in ilist[0] */
 initialize(m);
 sclear(0,1);
 readim(200,sy,200,200,t4,"nocom")       /* display original face */
 text(200,10,0,1,t4);
 if (version == 1)
  printf("/n Save in dbase? (Y/N) ) ");
   scanf ("%s",t3);
   if (ch[0] == 'y'    ch[0] -- 'Y')
    printf("n enter name of subject (up to 10 letters) /n)";
    scanf("%s",t3);
    p = 0; /* highest existing version # for this subject */
    for (n=1; n(k+1; n++)
     if (strcmp(ilist[n].name,t3) == 0)

k = k + 1;
p = p + 1;
ilist[k].name[0] = '/0';
strcat(ilist[k].name,t3;
ilist[k]num = p;
for (w=1; w(7; w++)
   ilist[k].winx[w] = ilist 0].winx[w];
   ilist[k].winy w] = ilist[0].winy[w];

t5[0] = '/0';
strcat(t5,"[face.dbase]/0");
strcat(t5,ilist[k].name;
strcat(t5,".img;/0"
saveim(200,sy,dx,dy,0,t5,"nocomm");
writefile("[face.dbase]others.dat'1",ilist,k);

else
 if (m (nf)
  printf("/n Forget about rest of faces and return to main menu? (Y/N) )";
   scanf("%s",ch);
   if (ch[0] == 'y'    ch[0] == 'Y')
    return;
```

```
recognize(0);                    /* pass in gestalt values of ilist[0] */
delet(t2)
delete(t4)
cls();

else
   printf("/n face not found.");
   prtc();

nf = sx = sy = 0;
fx = fy = 511;
return;

/******************************************************************/ static int results [257][5];
static int list[0]; /* list of id#s ordered by distances in list2 */
static double [0];list2[101];/* total distances (for all windows) */
static double v[101][7]; /* v[id][w] = distance from person #id to
       unknown person for window #w (Russel), 1985:4-40a)  */

/******************************************************************/
recognize(num)          /*from REMID.FR 06/03/86 by R. Russel */
 int num; /* the position in ilist[] of gestalt values to use. */ char t8[30];
double gix,gi,gux,guy,sigix,sigiy,a,b,c,most;
int id,w,m,n,j,confid,test;
double p[7] =   10.0,1.0,1.5,2.0,3.0,1.0 ; /* window performance factors
           (update after training and testing with sufficient samples  */
                 /* note: p[0] is used for total of factors */
printf("/n/n/n Now tring to recognize subject in top half of screen./")
printf("/n Presently trained with %d subjects.",(i/4));

for (w=1; w(7; w++)
 for (id=1; id((i/4)+1; id++)
  m = id*4 - 3;
  gix = (double) (tlist[m].winx[w] + tlist[m+1].winx[w] + tlist[m+2].winx[w]
                    + tlist[m+3].winx[w]) )4.0;
  giy = (double) (tlist[m].winy[w] + tlist[m+1].winy[w] + tlist[m+2].winy[w]
                    + tlist[m+3].winy[w]) )4.0;
  gux = (double) ilist[num].winx[w];
  guy = (double) ilist[num].winy[w];
  sigix = ( (double) (abs(gix-tlist[m].winx[w]*abs(gix-tlist[m].winx[w]+
           abs(gix-tlist[m+2].winx[w]*abs(gix-tlist[m+1].winx[w]+
           abs(gix-tlist[m+2].winx[w]*abs(gix-tlist[m+2].winx[w]+
           abs(gix-tlist[m+3].winx[w]*abs(gix-tlist[m+3].winx[w])) )/4.0;
  sigix = sqrt(sigix);
  if(sigiy ( .5) sigix =.5;

sigiy = ( (double) (abs(giy-tlist[m].winy[w]*abs(giy-tlist[m].winy[w]+
           abs(giy-tlist[m+2].winy[w]*abs(giy-tlist[m+1].winy[w]+
           abs(giy-tlist[m+2].winy[w]*abs(giy-tlist[m+2].winy[w]+
           abs(giy-tlist[m+3].winy[w]*abs(giy-tlist[m+3].winy[w])) )/4.0;
  sigiy = sqrt(sigiy);
  if (sigiy ( .5) sigiy = .5;
   a = (gix-gux)*(gix-gux)/(4*sigixsigix);
   b = (giy-guy)*(giy-guy)/(4*sigiy*sigiy);
   c = a + b;
   v[id][w] = exp(-1.0+c/1.4) * p[w];

for (id=1; id((i/4)+1 id++)
  t[id] = 0.000000001;
  for (w=1; w(7; w++)
    t[id] += v[id][w];

t[id] = t[id]/p[0]; /* max t[id] = 1.0 when distance form id to unknown */
                                            /* individual = 0.0*/

/* now have all distances ordered by id#, need to order id#s by distance */
```

```
for (m=1; m(101; m++)
   list[m] = 0;
   list2[m] = 0.000000001;

for (m=1; m((i/4)+1; m++)
   most = 0.000000001;
   for (j=1; j(i/4)+1; j++)
      if (t[j] ) most)
         most = t[j];
         n = [j;]

list[m]    = n;         /* id # */
      list2[m] = t[n];        /* distance */
      t[n] = 0.000000001;

/* now have ordered list of candidates, need to display them */
test = 0;
if (list2[1] 0 0.001)
   printf("/n/n                        Candidate             Distance");
/*   printf("     Confidence");       */
   for (m=1; m(i/4)+1; m++)
      if(ilist2[m] == 0.001)
         if (m == 1)
            printf("/n 1st Choice:");
            t8[0] = '/0';
            strcat(t8,"face.dbase]/0");

strcat(t8,tlist[list[1]*4 - 3].name);
            strcat(t8,".pic/0");
            readim(50,286,200,200,t8,"nocomm");
            text(50,266,0,1,200,tlist[tlist[list[1]*4 - 3].name;
            test = 1;

if (m == 2)
      print(:/n2nd Choice:");
      t8[0] = '/0,';
      strcat(t8,[face.dbase]/0");
      strcat(t8,tlist[list[3]*4 - 3].name);
      strcat(t8,".pic/0");
      readim(200,286,200,tlist[list][2]*4 - 3].name);
      test = 2;

if (m == 3)
         printf(;/n 3rd Choice:");
         t8[0] = ,0,;
         strcat(t8,"[face.dbase]/0");
         strcat(t8,tlist[list[3]*4 -3.name);
         strcat(t8,".pic/0");
         readim(350,286,200,200,t8,"nocomm:);
         text(350,266,0,1,200,tlist[list[2]*4 - 3].name;
         test = 3;

if (m == 4) printf("/n    Others:");
      if (m ) 4) printf("/n              ")
/*    confid = based on distance of this candidate and
                     distances to next candidates */
/*    printf("%11s   %f",tlist[listm]*4 - 3].name,list2[m];
         printf("    %d",confid);*/ else m=200;

if (test == 0)
   printf("/n/n Could not find any more close enough candidates.");
   printf("/n The computer has never seen this person before.");

if ( test ( 3 && test != 0)
   printf('/n/n Could not find any close enough candidates.");
   if (test == 1) printf("/n only displayed 1 picture.");
   else printf("/n only displayed 2 pictures.");
```

```
prtc();
return;

/******************************************************************/ — —
```

The easiest way to get to know the AFRM is to sit down and use it. The AFRM will perform several second of hardware and software initialization and will them present the main menu. When you are done using the AFRM, return to this menu and select the QUIT option.

Two Things You Should Not Do

1. The AFRM needs to create temporary files now and then as a normal part of its operation. It will delete these files as soon as they are no longer needed. Since these files are created and deleted without informing the user, the user should avoid saving files with these temporary-file names. Never save faces in files named:
BNORM.IMG
ORIG.IMG
at some un-announced point in time YOU WILL LOSE THEM.

2. The AFRM has been designed to be fault tolerant. You can enter anything you want, at any prompt you want, and the AFRM should handle it. The AFRM will inform you if your input is invalid. The only entries not allowed are CTRL-C and CTRL-Y which terminate the program without going to the main menu option QUIT. These are not allowed because the ARM will not be able to save updated database files and because the user will be allowed into the FACE account here he shouldn'be (the AFRM won't cause an automatic log-out).

During normal AFRM operation this is not a concern for the user because the CTRL-C and CTRL-Y entries are disabled by a protection scheme. It is only mentioned here to remind Special Users (those who modify install or initialize the system) to re-install the protection scheme when they are done and to make them aware of the consequences of CTRL keys when protection is not in place.

There are several ways to input images into the AFRM and there is a sub-menu for all the options. This sub-menu is obtained by selecting main menu option #1. Most of the menu options are self-explanatory and so minimum detail is given here.

0: Return to Main Menu
1: Stationary Target—Allows acquisition of a 512×480 image from the camera.
2: Moving Target—Acquires a background scene from the camera (nobody in it), then acquires a second scene (with subject). The AFRM will provide the rectangular area that is different in the two scenes. This target area is all that is processed by the face locator (if locator is selected) and so the face locator will be faster than it would be for a full size scene.
3: Load From —Allows user to load a previously stored image (for example, an image stored in the user's personal account on SMV2A).
4: Save in [FACE]—You can save images in this account if desired but please reserve the space in this account for images that are useful to everybody.
5: Set Camera Port—The default port is (0) and this allows use of the Dage camera. The two General Electric cameras are connected to ports (1) and (2).
6: Camera Check—Allows continuous acquisition of images so you can position and focus the camera.
7: Re-initialize Hardware—Go back to default camera port, clear the screen, etc.

Main menu option #2 runs the face location algorithm. This algorithm will look for faces in the image on the screen and save all it finds to temporary files.

Main menu option #3 only works after a face(s) was found by option #2. If no face(s) was found then this option will return to the main menu. This option runs the gestalt algorithm on the first face found by option #2. Then it runs there cognition algorithm on that face. During recognition the user is allowed to save the face and its gestalt data in the database. There is no other time when a new face and its gestalt data are available for saving in the database so save it NOW if you want it, otherwise you will have to Gestalt it again later (faces are easily deleted from the database if you change your mind later). If more than one face was found in option #2 than all faces will be gestalted and identified in the order found.

Several main menu options are discussed below in Table 3 because they all have something to do with using and changing the debase

TABLE 3

Display Contents of Database

Delete a Subject—To "delete a subject" means to delete the training file for this subject. The actual images and gestalt values can still be saved in the . IMG section (files it is not trained on) and the AFRM can be retrained with this subject later. You may also delete this subject from the database altogether if desired.

Delete an Image—This option allows the deletion of single images (files that the AFRM is not trained on) from the database.

Train—This allows the user to train the database with 4 files from the . IMG section of the database. The files must all have the same name and must have different version numbers. To exit this option at any time, enter a negative version number.

Fault tolerance is really evident in the AFRM because it is important to maintain a correct database. The AFRM constantly checks user inputs for validity and gives out pertinent information when it finds a mistake. For example, suppose, it is decided to train the AFRM with the name Smith, version numbers 1, 2, 3, and 4. The AFRM will verify that the name you enter exists in the . IMG section and that it does not exist in the trained section. It will verify that files exist in the trained section. It will verify that files exist for all the versions you type in and that you have not typed the same version number more than once. If you make a mistake and wish to exit to the main menu, you are allowed to so at any time.

The Total System option allows the user to run all AFRM algorithms together starting at image acquisition and ending with recognition. This option is run as follows:

1. Run the "Camera Check" option and set the camera up to take a full body picture of a standing person.

Then ensure nobody is standing in the filed of view of the camera.
2. Select the total system option.
3. Select the camera port desired. After a couple seconds, the screen will go black as the camera continually acquires images and the itex board applies real-time subtraction.
4. When the screen is black, have a subject walk into the field of view of the camera, turn and stare at the camera, and stand still for a few seconds. As soon as the AFRM "sees" the subject it will snap a picture and begin to look for a face.
(There is no sharpening option to worry about about here.) If a face is found, then the AFRM will gestalt it and try to recognize the individual. (There is no save option here.)
5. After recognition, the user will be asked if the whole process should repeat.

While the invention has been described in its presently preferred embodiment it is understood that the words which have been used are words of description rather than words of limitation and that changes within the purview of the appended claims may be made without departing from the scope and spirit of the invention in its broader aspects.

What is claimed is:

1. A face recognition video system which locates and recognizes a human face in a video scene which has an input scene size of about 512 by 480 pixels and a random background, wherein said face recognition video system identifies said human face with a set of stored characteristics which are correlated with known human faces, said face recognition video system comprising:
   a camera which receives said video scene and outputs it in an analog electrical signal;
   a means for converting analog signals into digital signals, said converting means receiving and converting said analog electrical signal from said camera into a digital electrical signal;
   a means for applying an elliptical mask to said video scene around a location of said human face for recognizing and identifying human faces, said applying means receiving said digital electrical signal from said converting means and locating said human face within that video scene by searching for and extracting detected facial characteristics within said video scene, said applying means then applying said elliptical mask around the location of the human face and defining a detected gestalt-face within said video scene with a minimum facial size of 64 by 64 pixels by identifying said detected facial characteristics using the detected facial characteristics of whole human faces by comparing said detected facial characteristics of said detected gestalt face with said set of stored face characteristics and outputting a name associated with the stored face characteristics which successfully correlates with said detected gestalt face, wherein said applying means comprises a Micro Vax computer which has a memory which has said set of stored face characteristics stored therein along with a set of names of said known human faces, said Micro Vax computer being electrically connected with said converting means to receive said digital electrical signal thereby, said Micro Vax computer searching said video scene for detected facial characteristics beginning with a search for a pair of eyes in said video scene, said Micro Vax computer outputting a signal to indicate that there are no human faces in said video scene when no pair of eyes are detected, said Micro Vax computer continuing to look for said facial characteristics once a human face is detected until it has sufficient detected facial characteristics to form said detected gestalt face which may be compared with said set of stored face characteristics and to identify said human face in said video scene thereby; and
   and a means for displaying said name produced by said applying means, said displaying means being electrically connected with said applying means to receive said name therefrom.

* * * * *